United States Patent [19]

Barnes et al.

[11] Patent Number: 5,710,102

[45] Date of Patent: Jan. 20, 1998

[54] DIFLUOROVINYLSILANE INSECTICIDAL AND ACARICIDAL AGENTS

[75] Inventors: Keith Douglas Barnes, Newtown, Pa.; Yulin Hu, Plainsboro, N.J.

[73] Assignee: American Cyanamid Company, Madison, N.J.

[21] Appl. No.: 805,104

[22] Filed: Feb. 24, 1997

[51] Int. Cl.$^6$ .................. A01N 55/10; C07F 7/12
[52] U.S. Cl. .................. 504/193; 556/488; 546/14; 548/110
[58] Field of Search .................. 504/193; 556/488; 546/14; 548/110

[56] References Cited

U.S. PATENT DOCUMENTS

| | | | |
|---|---|---|---|
| 4,864,027 | 9/1989 | Shubert et al. | 546/14 |
| 5,248,834 | 9/1993 | Elliott et al. | 549/330 |

FOREIGN PATENT DOCUMENTS

WO 88/01271  2/1988  Japan.

*Primary Examiner*—Jane Fan
*Attorney, Agent, or Firm*—Joseph M. Mazzarese

[57] ABSTRACT

Difluorovinylsilane compounds having the structural formula I

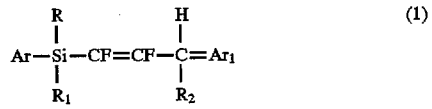

and compositions thereof, and methods for the control of insect and acarid pests and protection of plants.

17 Claims, No Drawings

DIFLUOROVINYLSILANE INSECTICIDAL AND ACARICIDAL AGENTS

This application claims priority from copending provisional application Ser. No. 60/013,596 filed on Mar. 18, 1996.

BACKGROUND OF THE INVENTION

Insect and acarid pests destroy growing and harvested crops. In the Unites States, agronomic crops must compete with thousands of those pests. In particular, tobacco budworms and southern armyworms are especially devastating to crops.

Tobacco budworms cause tremendous economic losses in agronomic crops. In particular, budworms devastate cotton crops by feeding on green bolls. Control of budworms is complicated by their resistance to many common insecticides, including organophosphates, carbamates and pyrethroids.

In spite of the commercial insecticides and acaricides available today, damage to crops, both growing and harvested, caused by insect and acarid pests still occurs. Accordingly, there is ongoing research to create new and more effective insecticidal and acaricidal agents.

Certain fluoroolefin and silane compounds are known to possess insecticidal and acaricidal activity (see, e.g., U.S. Pat. Nos. 4,864,027; 5,248,834 and WO 88/01271). However, none of the compounds disclosed in those patents and patent application are within the scope of the present invention.

SUMMARY OF THE INVENTION

The present invention comprises difluorovinylsilane compounds of the structural formula I

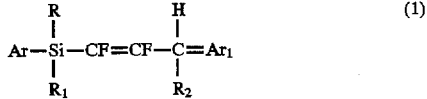

wherein

Ar is phenyl optionally substituted with any combination of from one to three halogen, $C_1$–$C_4$alkyl, $C_1$–$C_4$haloalkyl, $C_1$–$C_4$alkoxy, $C_1$–$C_4$haloalkoxy, cyano, nitro, $CO_2R_3$, $C(O)R_4$, $S(O)_nR_5$ or $NR_6R_7$ groups, 1- or 2-naphthyl optionally substituted with any combination of from one to three halogen, $C_1$–$C_4$alkyl, $C_1$–$C_4$haloalkyl, $C_1$–$C_4$alkoxy, $C_1$–$C_4$haloalkoxy, cyano, nitro, $CO_2R_3$, $C(O)R_4$, $S(O)_nR_5$ or $NR_6R_7$ groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy, $C_1$–$C_4$haloalkoxy, cyano, nitro, $CO_2R_3$, $C(O)R_4$, $S(O)_n R_5$ or $NR_6R_7$ groups;

R and $R_1$ are each independently hydrogen, $C_1$–$C_4$alkyl or $C_3$–$C_5$cycloalkyl;

$R_2$ is hydrogen, cyano, $C_1$–$C_4$alkyl, $C_1$–$C_4$haloalkyl, $C_1$–$C_4$alkoxy, $C_1$–$C_4$haloalkoxy or halogen;

$Ar_1$ is phenoxyphenyl optionally substituted with any combination of from one to five halogen, $C_1$–$C_4$alkyl, $C_1$–$C_4$haloalkyl, $C_1$–$C_4$alkoxy, $C_1$–$C_4$haloalkoxy, cyano, nitro, $CO_2R_8$, $C(O)R_9$, $S(O)_mR_{10}$ or $NR_{11}R_{12}$ groups, phenyl optionally substituted with any combination of from one to five halogen, $C_1$–$C_4$alkyl, $C_1$–$C_4$haloalkyl, $C_1$–$C_4$alkoxy, $C_1$–$C_4$haloalkoxy, cyano, nitro, $CO_2R_8$, $C(O)R_9$, $S(O)_mR_{10}$ or $NR_{11}R_{12}$ groups, biphenyl optionally substituted with any combination of from one to five halogen, $C_1$–$C_4$alkyl, $C_1$–$C_4$haloalkyl, $C_1$–$C_4$alkoxy, $C_1$–$C_4$haloalkoxy, cyano, nitro, $CO_2R_8$, $C(O)R_9$, $S(O)_mR_{10}$ or $NR_{11}R_{12}$ groups, phenoxypyridyl optionally substituted with any combination of from one to five halogen, $C_1$–$C_4$alkyl, $C_1$–$C_4$haloalkyl, $C_1$–$C_4$alkoxy, $C_1$–$C_4$haloalkoxy, cyano, nitro, $CO_2R_8$, $C(O)R_9$, $S(O)_mR_{10}$ or $NR_{11}R_{12}$ groups, benzylpyridyl optionally substituted with any combination of from one to five halogen, $C_1$–$C_4$alkyl, $C_1$–$C_4$haloalkyl, $C_1$–$C_4$alkoxy, $C_1$–$C_4$haloalkoxy, cyano, nitro, $CO_2R_8$, $C(O) R_9$, $S(O)_mR_{10}$ or $NR_{11}R_{12}$ groups, benzylphenyl optionally substituted with any combination of one to five halogen, $C_1$–$C_4$alkyl, $C_1$–$C_4$haloalkyl, $C_1$–$C_4$alkoxy, $C_1$–$C_4$haloalkoxy, cyano, nitro, $CO_2R_8$, $C(O)R_9$, $S(O)_mR_{10}$ or $NR_{11}R_{12}$ groups, 1- or 2-naphthyl optionally substituted with any combination of from one to three halogen, $C_1$–$C_4$alkyl, $C_1$–$C_4$haloalkyl, $C_1$–$C_4$alkoxy, $C_1$–$C_4$haloalkoxy, cyano, nitro, $CO_2R_9$, $C(O)R_9$, $S(O)_mR_{10}$ or $NR_{11}R_{12}$ groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy, $C_1$–$C_4$haloalkoxy, cyano, nitro, $CO_2R_8$, $C(O)R_9$, $S(O)_m R_{10}$ or $NR_{11}R_{12}$ groups;

m and n are each independently an integer of 0, 1 or 2;

$R_3$ and $R_8$ are each independently hydrogen, $C_1$–$C_4$alkyl, benzyl, phenyl or an alkali metal, alkaline earth metal, manganese, copper, zinc, cobalt, silver or nickel cation;

$R_4$ and $R_5$ are each independently hydrogen, $C_1$–$C_4$alkyl, benzyl or phenyl;

$R_5$ and $R_{10}$ are each independently $C_1$–$C_4$alkyl or $C_1$–$C_4$haloalkyl; and $R_6$, $R_7$, $R_{11}$ and $R_{12}$ are each independently hydrogen, $C_1$–$C_4$alkyl, phenyl or benzyl, and the optical isomers thereof, and the cis and trans isomers thereof.

This invention also comprises compositions containing a compound of formula I, and methods for using those compounds and compositions. Advantageously, it has been found that the difluorovinylsilane compounds of the present invention, and compositions containing them, are useful for the control of insect and acarid pests, especially useful for the control of tobacco budworms and southern armyworms. The compounds and compositions of this invention are also useful for the protection of plants from damage caused by insect and acarid attack and infestation.

It is an object of the present invention to provide compounds which are highly effective for the control of insect and acarid pests.

It is also an object of the present invention to provide a method for the control of insect and acarid pests.

It is a further object of this invention to provide a method for the protection of growing and harvested crops from damage caused by insect and acarid attack and infestation.

Other objects of the present invention will be apparent to one skilled in the art from the detailed description thereof set forth below.

DETAILED DESCRIPTION OF THE INVENTION

One aspect of the present invention is a method for the control of insect or acarid pests which comprises contacting said pests or their food supply, habitat or breeding grounds with a pesticidally effective amount of a difluorovinylsilane compound of formula I.

Another aspect of the present invention is a method for the protection of growing plants from attack or infestation by insect or acarid pests which comprises applying to the foliage of the plants, or to the soil or water in which they are growing, a pesticidally effective amount of a difluorovinylsilane compound of formula I.

The difluorovinylsilane compounds of the present invention have the structural formula I $$\begin{array}{c} R \quad\quad\quad H \\ | \quad\quad\quad | \\ Ar-Si-CF=CF-C=Ar_1 \\ | \quad\quad\quad | \\ R_1 \quad\quad\quad R_2 \end{array} \quad (1)$$

wherein Ar, $Ar_1$, R, $R_1$ and $R_2$ are as described hereinabove for formula I.

In formula I above, 5- and 6-membered heteroaromatic rings include, but are not limited to, pyridyl, pyrazolyl, imidazolyl, triazolyl, isoxazolyl, tetrazolyl, pyrazinyl, pyridazinyl, triazinyl, furanyl, thienyl and thiazolyl rings each optionally substituted as described in formula I above.

Exemplary of halogen hereinabove are fluorine, chlorine, bromine and iodine. The terms "$C_1$–$C_4$haloalkyl" and "$C_1$–$C_4$haloalkoxy" are defined as a $C_1$–$C_4$alkyl group and a $C_1$–$C_4$alkoxy group substituted with one or more halogen atoms, respectively.

Preferred formula I difluorovinylsilane compounds of the present invention are those wherein Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R and $R_1$ are each independently $C_1$–$C_4$alkyl;

$R_2$ is hydrogen, cyano, $C_1$–$C_4$alkyl, $C_1$–$C_4$haloalkyl, $C_1$–$C_4$alkoxy, $C_1$–$C_4$haloalkoxy or fluorine; and $Ar_1$ is 3-phenoxyphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

More preferred insecticidal and acaricidal agents of the present invention are those wherein Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R and $R_1$ are methyl;

$R_2$ is hydrogen; and $Ar_1$ is 3-phenoxyphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups. Formula I compounds of this invention which are particularly effective insecticidal agents include 1-[(p-chlorophenyl)dimethylsilyl]-1,2-difluoro-3-(m-phenoxyphenyl)-1-propene, (Z)-;

1-[(p-chlorophenyl)dimethylsilyl]-1,2-difluoro-3-(4-fluoro-3-phenoxyphenyl)-1-propene, (Z)-;

1-[(p-ethoxyphenyl)dimethylsilyl]-1,2-difluoro-3-(m-phenoxyphenyl)-1-propene, (Z)-;

1-[(p-ethoxyphenyl)dimethylsilyl]-1,2-difluoro-3-(4-fluoro-3-phenoxyphenyl)-1-propene, (Z)-;

1-[(p-ethoxyphenyl)dimethylsilyl]-1,2-difluoro-3-(2-methyl-3-biphenylyl)-1-propene, (Z)-;

1,2-difluoro-1-[(p-fluorophenyl)dimethylsilyl]-3-(m-phenoxyphenyl)-1-propene, (Z)-;

3-[3-(p-chlorophenoxy)phenyl]-1-[(p-ethoxyphenyl)dimethylsilyl]-1,2-difluoro-1-propene, (Z)-; and 1,2-difluoro-3-(p-fluoro-3-phenoxyphenyl)-1-[(p-fluorophenyl)dimethylsilyl]-1-propene, (Z)-, among others.

Advantageously, it has been found that the formula I compounds of the present invention are especially useful for the control of tobacco budworms and southern armyworms.

Difluorovinylsilyl compounds of the present invention wherein the double bond is in the (Z)- configuration may be prepared, as indicated as Flow Diagram I, by reacting an arylmetallic compound of formula II with a dichlorosilane compound of formula III to form an arylchlorosilane compound of formula IV, reacting the arylchlorosilane compound with bromotrifluoroethylene to form a [(trifluorovinyl)silyl]aryl compound of formula V, reducing the formula V compound with a reducing agent such as lithium aluminum hydride to form a [(1,2-difluorovinyl)silyl]aryl compound of formula VI which is predominantly in the (Z)- configuration, reacting the formula VI compound with a lithium base such as butyllithium or lithium tetramethyl piperidine and zinc chloride or tributyltin chloride to form an intermediate compound, and reacting the intermediate compound with an α-(bromomethyl)aryl compound of formula VII optionally in the presence of a catalytic amount of a catalyst such as tetrakis(triphenylphosphine)palladium (O).

FLOW DIAGRAM I

Ar-M
(II)
(M = Mg or Li)

↓

$$\begin{array}{c} R \quad\quad R_1 \\ \diagdown \;\; \diagup \\ Si \\ \diagup \;\; \diagdown \\ Cl \quad\quad Cl \end{array} \quad (III)$$

↓

$$\begin{array}{c} R \quad\quad R_1 \\ \diagdown \;\; \diagup \\ Si \\ \diagup \;\; \diagdown \\ Ar \quad\quad Cl \end{array} \quad (IV)$$

↓

$$\begin{array}{c} Br \quad\quad F \\ \diagdown = \diagup \\ \diagup \quad\quad \diagdown \\ F \quad\quad F \end{array}$$

↓

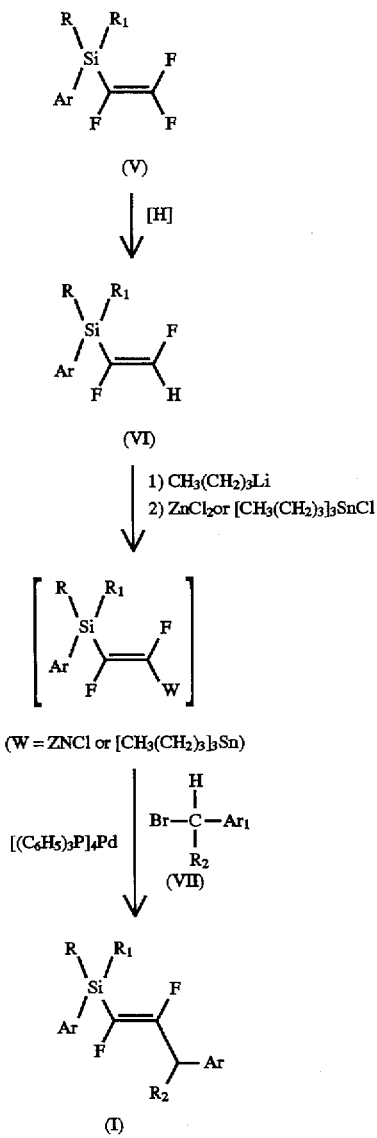

Formula I compounds wherein the double bond is in the (E)- configuration may be prepared by isomerizing the [(1,2-difluorovinyl)silyl]aryl compound of formula VI which is predominantly in the (Z)- configuration using conventional procedures such as exposure to light to form a [(1,2-difluorovinyl)silyl]aryl compound which is predominantly in the (E)- configuration, and reacting the resultant [(1,2-difluorovinyl)silyl]aryl compound as described above for the formula VI compound to produce the desired formula I compound wherein the double bond is in the (E)- configuration.

Advantageously, certain formula I compounds of this invention may be derivatized by conventional procedures known in the art to produce other compounds of formula I.

The difluorovinylsilane compounds of the present invention are effective for controlling insect and acarid pests. Those compounds are also effective for protecting growing or harvested crops from damage caused by insect and acarid attack and infestation.

Insects controlled by the difluorovinylsilane compounds of this invention include Lepidoptera such as tobacco budworms, cabbage loopers, cotton boll worms, beet armyworms, southern armyworms and diamondback moths; Homoptera such as aphids, leaf hoppers, plant hoppers and white flies; Thysanoptera such as thrips; Coleoptera such as boll weevils, Colorado potato beetles, southern corn rootworms, western corn rootworms and mustard beetles; and Orthoptera such as locusts, crickets, grasshoppers and cockroaches. Acarina controlled by the compounds of this invention include mites such as two-spotted spider mites, carmine spider mites, banks grass mites, strawberry mites, citrus rust mites and leprosis mites. Advantageously, it has been found that the compounds of the present invention are especially effective against tobacco budworms and southern armyworms.

In practice generally about 10 ppm to about 10,000 ppm and preferably about 100 ppm to about 5,000 ppm of a formula I difluorovinylsilane, dispersed in water or another liquid carrier, is effective when applied to plants or the soil in which the plants are growing to protect the plants from insect and acarid attack and infestation.

The difluorovinylsilane compounds of this invention are also effective for controlling insect and acarid pests when applied to the foliage of plants and/or to the soil or water in which said plants are growing in sufficient amount to provide a rate of about 0.1 kg/ha to 4.0 kg/ha of active ingredient.

While the compounds of this invention are effective for controlling insect and acarid pests when employed alone, they may also be used in combination with other biological chemicals, including other insecticides and acaricides. For example, the formula I compounds of this invention may be used effectively in conjunction or combination with pyrethroids, phosphates, carbamates, cyclodienes, endotoxin of bacillus thuringiensis (Bt), formamidines, phenol tin compounds, chlorinated hydrocarbons, benzoylphenyl ureas, pyrroles and the like.

The compounds of this invention may be formulated as emulsifiable concentrates, flowable concentrates or wettable powders which are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations or compositions of the present invention include a compound of the invention (or combinations thereof) admixed with one or more agronomically acceptable inert, solid or liquid carriers. These compositions contain a pesticidally effective amount of said compound or compounds, which amount may vary depending upon the particular compound, target pest, and method of use. Those skilled in the art can readily determine what is a pesticidally effective amount without undue experimentation.

In order to facilitate a further understanding of the invention, the following examples are presented primarily for the purpose of illustrating more specific details thereof. The invention should not be deemed limited by the examples as the full scope of the invention is defined in the claims.

EXAMPLE 1

Preparation of p-(Chlorodimethylsilyl)phenetole

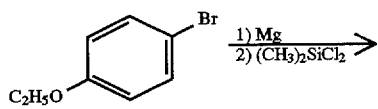

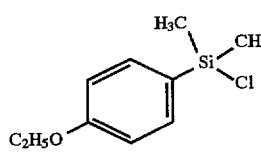

A solution of p-bromophenetole (40.2 g, 0.2 mol) in tetrahydrofuran is added dropwise to a stirred mixture of magnesium turnings (4.86 g, 0.2 mol) in tetrahydrofuran under nitrogen. After the addition is complete, the reaction mixture is stirred at 60° C. for 45 minutes, cooled to room temperature and added dropwise to a solution of dichlorodimethylsilane (25.8 g, 0.2 mol) in tetrahydrofuran while maintaining the temperature below −60° C. The resultant reaction mixture is stirred at −65° C. for 15 minutes, stirred overnight at room temperature, diluted with hexanes, filtered through a pad of diatomaceous earth, concentrated in vacuo, diluted with additional hexanes and filtered through a second pad of diatomaceous earth. The resultant filtrate is concentrated in vacuo to obtain a brown liquid which is distilled to give the title product as a clear liquid (22.2 g, bp 81°–87° C./0.4 mm Hg).

Using essentially the same procedure, the following compounds are obtained:

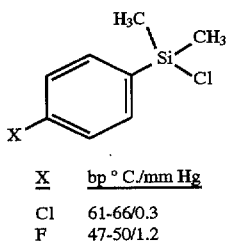

| X | bp ° C./mm Hg |
|---|---|
| Cl | 61-66/0.3 |
| F | 47-50/1.2 |

EXAMPLE 2

Preparation of p-[(Trifluorovinyl)dimethylsilyl]phenetole

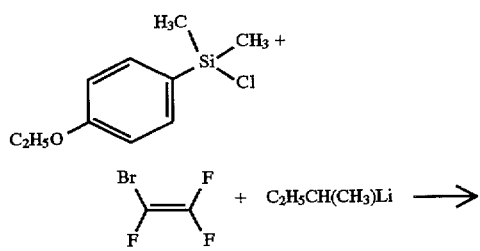

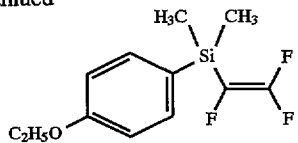

A −30° C. solution of bromotrifluoroethylene (7.15 g, 0.044 mol) in ether is treated with p-(chlorodimethylsilyl) phenetole (9.54 g, 0.044 mol), cooled to −65° C., treated dropwise with a 1.3M solution of sec-butyllithium in cyclohexane (34.2 mL, 0.044 mol) while maintaining the temperature below −60° C., stirred at −65° C. for 5 hours, stirred at room temperature overnight, cooled to 0° C., treated with dilute hydrochloric acid, and diluted with ether. The organic phase is separated, washed with brine, dried over anhydrous magnesium sulfate and concentrated in vacuo to obtain a residue which is distilled to give the title product as a clear liquid (7.66 g, bp 84°–92° C./0.8 mm Hg).

Using essentially the same procedure, the following compounds are obtained:

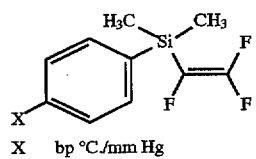

| X | bp °C./mm Hg |
|---|---|
| Cl | 64–70/1.2 |
| F | 58–62/2-3 |

EXAMPLE 3

Preparation of p-[(1,2-Difluorovinyl)dimethylsilyl] phenetole

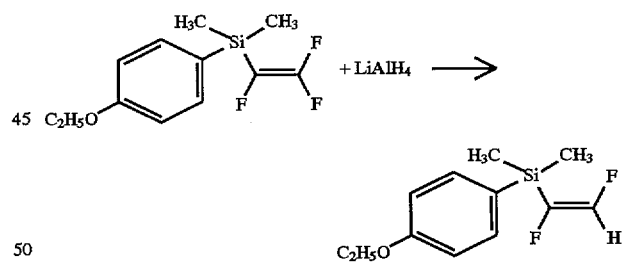

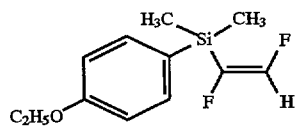

A solution of p-[(trifluorovinyl)dimethylsilyl]phenetole (12.0 g, 0.046 mol) in tetrahydrofuran is added dropwise to a stirred mixture of lithium aluminum hydride (1.75 g, 0.046 mol) in tetrahydrofuran at −5° C. The resultant reaction mixture is stirred at room temperature for 4 hours, cooled to 0° C., treated sequentially with ethyl acetate, water and dilute hydrochloric acid, and diluted with additional ether and dilute hydrochloric acid. The organic phase is separated, washed with brine, dried over anhydrous magnesium sulfate and concentrated in vacuo to give the title product as a yellow liquid (10.76 g) which is identified by $^1$H NMR analysis as a 9:1 mixture of Z:E isomers.

Using essentially the same procedure, the following compounds are obtained:

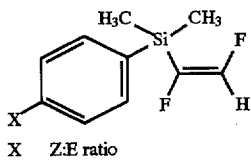

| X  | Z:E ratio |
|----|-----------|
| Cl | 9:1       |
| F  | 19:1      |

EXAMPLE 4

Preparation of 1-[(p-Ethoxyphenyl)dimethylsilyl]-1,2-difluoro-3-(4-fluoro-3-phenoxphenyl)-1-propene, (Z)-

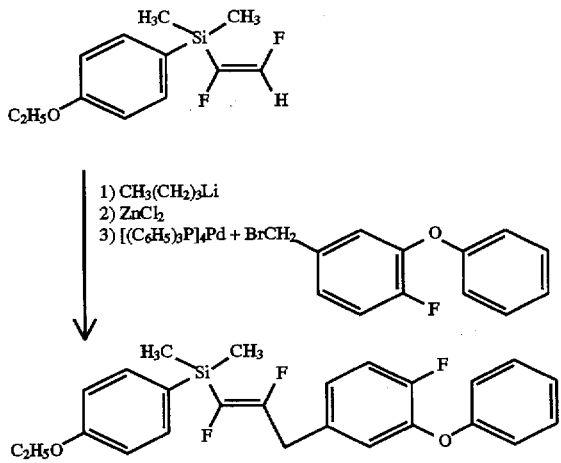

A solution of p-[(1,2-difluorovinyl)dimethylsilyl] phenetole having a Z:E ratio of 9:1 (2.0 g, 0.0083 mol) in tetrahydrofuran is cooled to −65° C., treated dropwise with a 2.5M solution of butyllithium in hexanes (3.30 mL) while maintaining the temperature below −60° C., stirred at −65° C. for 30 minutes, treated dropwise with a 0.5M solution of zinc chloride in tetrahydrofuran (16.5 mL, 0.0083 mol) while maintaining the temperature below −60° C., stirred at −65° C. for 30 minutes, treated sequentially with a solution of α-bromo-4-fluoro-3-phenoxytoluene (1.71 g, 0.0064 mol) in tetrahydrofuran and a solution of tetrakis (triphenylphosphine)palladium(O) (0.22 g, 0.0002 mol) in tetrahydrofuran, stirred at room temperature overnight and diluted with ether. The resultant organic solution is washed sequentially with dilute hydrochloric acid and brine, dried over anhydrous magnesium sulfate and concentrated in vacuo to obtain a residue. The residue is subjected to Kugelrohr distillation to remove volatiles. Flash chromatography of the resultant oil using silica gel and a 15:100 methylene chloride/hexanes solution provides an oil which is further purified on alumina using a 1:100 ethyl acetate/hexanes solution to give the title product as a colorless syrup (0.24 g) which is identified by NMR spectral analyses.

Using essentially the same procedure, the following compounds are obtained:

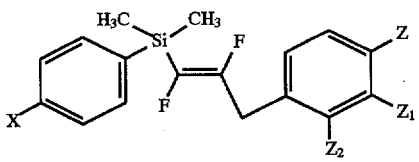

| X       | Z | $Z_1$         | $Z_2$  |
|---------|---|---------------|--------|
| Cl      | H | $OC_6H_5$     | H      |
| Cl      | F | $OC_6H_5$     | H      |
| $OC_2H_5$ | H | $OC_6H_5$   | H      |
| F       | H | $OC_6H_5$     | H      |
| $OC_2H_5$ | H | $C_6H_5$    | $CH_3$ |
| F       | F | $OC_6H_5$     | H      |
| $OC_2H_5$ | H | $OC_6H_4\text{-p-Cl}$ | H |

EXAMPLE 5

Insecticidal and acaricidal evaluation of test compounds

Test solutions are prepared by dissolving the test compound in a 35% acetone in water mixture to give a concentration of 10,000 ppm. Subsequent dilutions are made with water as needed.

*Spodoptera eridania*, 3rd instar larvae, douthern armyworm (SAW)

A Sieva lima bean leaf expanded to 7–8 cm in length is dipped in the test solution with agitation for 3 seconds and allowed to dry in a hood. The leaf is then placed in a 100×10 mm petri dish containing a damp filter paper on the bottom and ten 3rd instar caterpillars. At 5 days, observations are made of mortality, reduced feeding, or any interference with normal molting.

*Diabrotica virgifera virgifera* Leconte, 3rd instar western corn rootworm (WCR)

One cc of fine talc is placed in a 30 mL wide-mouth screw-top glass jar. One mL of the appropriate acetone test solution is pipetted onto the talc so as to provide 1.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed mechanically. Following this, ten 3rd instar rootworms are added to each jar and the jars are loosely capped to allow air exchange for the larvae. The treatments are held for 5 days when mortality counts are made. Missing larvae are presumed dead, since they decompose rapidly and can not be found. The concentrations of active ingredient used in this test correspond approximately to 50 kg/ha.

*Heliothis virenscens*, 3rd instar tobacco budworm (TBW)

Cotton cotyledons are dipped in the test solution and allowed to dry in a hood. When dry, each is cut into quarters and ten sections are placed individually in 30 mL plastic medicine cups containing a 5 to 7 mm long piece of damp dental wick. One 3rd instar caterpillar is added to each cup and a cardboard lid placed on the cup. Treatments are maintained for 3 days before mortality counts and estimates of reduction in feeding damage are made.

*Aphis fabae*, mixed instar, bean aphid (BA)

Pots containing single nasturtium plants (Tropaeolum sp.) about 5 cm tall are infested with about 100–200 aphids one day before the test. Each pot is sprayed with the test solution for 2 revolutions of a 4 rpm turntable in a hood. The spray is directed to give complete coverage of the plants and aphids. The sprayed pots are set on their sides on white trays and held for 2 days, following which mortality estimates are made.

*Tetranychus urticae* (OP-resistant strain), 2-spotted spider mite (TSM)

Sieva lima bean plants with primary leaves expanded to 7–8 cm are selected and cut back to one plant per pot. A small piece is cut from an infested leaf taken from the main colony and placed on each leaf of the test plants. This is done about 2 hours before treatment to allow the mites to move over to the test plant to lay eggs. The size of the cut, infested leaf is varied to obtain about 100 mites per leaf. At the time of test treatment, the piece of leaf used to transfer the mites is removed and discarded. The newly-infested plants are dipped in the test solution for 3 seconds with agitation and set in the hood to dry. After 2 days, one leaf is removed and mortality counts are made.

The tests are rated according to the scale shown below and the data obtained are shown in Table I.

Compounds employed in the above-described evaluations are given a compound number and identified by name. Data in Table I are reported by compound number.

| Rating Scale | |
|---|---|
| 0 = no effect | 5 = 56–65% kill |
| 1 = 10–25% kill | 6 = 66–75% kill |
| 2 = 26–35% kill | 7 = 76–85% kill |
| 3 = 36–45% kill | 8 = 86–99% kill |
| 4 = 46–55% kill | 9 = 100% kill |
| — = not tested | |

Compounds Evaluated as Insecticidal and Acaricidal Agents

| Compound Number | |
|---|---|
| 1 | 1-[(p-Chlorophenyl)dimethylsilyl]-1,2-difluoro-3-(m-phenoxyphenyl)-1-propene, (Z)- |
| 2 | 1-[(p-Chlorophenyl)dimethylsilyl]-1,2-difluoro-3-(4-fluoro-3-phenoxyphenyl)-1-propene, (Z)- |
| 3 | 1-[(p-Ethoxyphenyl)dimethylsilyl]-1,2-difluoro-3-(m-phenoxyphenyl)-1-propene, (Z)- |
| 4 | 1-[(p-Ethoxyphenyl)dimethylsilyl]-1,2-difluoro-3-(4-fluoro-3-phenoxyphenyl)-1-propene (Z)- |
| 5 | 1-[(p-Ethoxyphenyl)dimethylsilyl]-1,2-difluoro-3-(2-methyl-3-biphenylyl)-1-propene, (Z)- |

We claim:
1. A compound having the structural formula

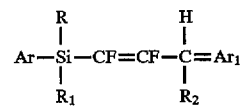

wherein
Ar is phenyl optionally substituted with any combination of from one to three halogen, $C_1$–$C_4$alkyl, $C_1$–$C_4$haloalkyl, $C_1$–$C_4$alkoxy, $C_1$–$C_4$haloalkoxy, cyano, nitro, $CO_2R_3$, $C(O)R_4$, $S(O)_nR_5$ or $NR_6R_7$ groups, 1- or 2-naphthyl optionally substituted with any combination of from one to three halogen, $C_1$–$C_4$alkyl, $C_1$–$C_4$haloalkyl, $C_1$–$C_4$alkoxy, $C_1$–$C_4$haloalkoxy, cyano, nitro, $CO_2R_3$, $C(O)R_4$, $S(O)_nR_5$ or $NR_6R_7$ groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy, $C_1$–$C_4$haloalkoxy, cyano, nitro, $CO_2R_3$, $C(O)R_4$, $S(O)_n R_5$ or $NR_6R_7$ groups;

R and $R_1$ are each independently hydrogen, $C_1$–$C_4$alkyl or $C_3$–$C_5$cycloalkyl;

$R_2$ is hydrogen, cyano, $C_1$–$C_4$alkyl, $C_1$–$C_4$haloalkyl, $C_1$–$C_4$alkoxy, $C_1$–$C_4$haloalkoxy or halogen;

$Ar_1$ is phenoxyphenyl optionally substituted with any combination of from one to five halogen, $C_1$–$C_4$alkyl, $C_1$–$C_4$haloalkyl, $C_1$–$C_4$alkoxy, $C_1$–$C_4$haloalkoxy, cyano, nitro, $CO_2R_8$, $C(O)R_9$, $S(O)_mR_{10}$ or $NR_{11}R_{12}$ groups, phenyl optionally substituted with any combination of from one to five halogen, $C_1$–$C_4$alkyl, $C_1$–$C_4$haloalkyl, $C_1$–$C_4$alkoxy, $C_1$–$C_4$haloalkoxy, cyano, nitro, $CO_2R_8$, $C(O)R_9$, $S(O)_mR_{10}$ or $NR_{11}R_{12}$ groups, biphenyl optionally substituted with any combination of from one to five halogen, $C_1$–$C_4$alkyl, $C_1$–$C_4$haloalkyl, $C_1$–$C_4$alkoxy, $C_1$–$C_4$haloalkoxy, cyano, nitro, $CO_2R_8$, $C(O)R_9$, $S(O)_mR_{10}$ or $NR_{11}R_{12}$ groups, phenoxypyridyl optionally substituted with any combination of from one to five halogen, $C_1$–$C_4$alkyl, $C_1$–$C_4$haloalkyl, $C_1$–$C_4$alkoxy, $C_1$–$C_4$haloalkoxy, cyano, nitro, $CO_2R_8$, $C(O)R_9$, $S(O)_mR_{10}$ or $NR_{11}R_{12}$ groups, benzylpyridyl optionally substituted with any combination of from one to five halogen, $C_1$–$C_4$alkyl, $C_1$–$C_4$haloalkyl, $C_1$–$C_4$alkoxy, $C_1$–$C_4$haloalkoxy, cyano, nitro, $CO_2R_8$, $C(O)R_9$, $S(O)_mR_{10}$ or $NR_{11}R_{12}$ groups,

TABLE I

| | Insecticidal And Acaricidal Evaluation Of Test Compounds | | | | | | | |
|---|---|---|---|---|---|---|---|---|
| Compound | SAW | | WCR | TBW | | BA | | TSM |
| Number | (300 ppm) | (100 ppm) | (50 ppm) | (300 ppm) | (100 ppm) | (300 ppm) | (100 ppm) | (300 ppm) |
| 1 | 9 | 9 | 9 | 9 | 9 | 7 | 7 | 2 |
| 2 | 9 | 9 | 9 | 9 | 9 | 8 | 9 | 3 |
| 3 | 9 | 9 | 9 | 9 | 9 | 8 | 8 | 0 |
| 4 | 9 | 9 | 9 | 9 | 9 | 8 | 8 | 0 |
| 5 | — | 9 | 9 | — | 8 | 8 | 0 | 0 | benzylphenyl optionally substituted with any combination of one to five halogen, $C_1-C_4$alkyl, $C_1-C_4$haloalkyl, $C_1-C_4$alkoxy, $C_1-C_4$haloalkoxy, cyano, nitro, $CO_2R_8$, $C(O)R_9$, $S(O)_mR_{10}$ or $NR_{11}R_{12}$ groups, 1- or 2-naphthyl optionally substituted with any combination of from one to three halogen, $C_1-C_4$alkyl, $C_1-C_4$haloalkyl, $C_1-C_4$alkoxy, $C_1-C_4$haloalkoxy, cyano, nitro, $CO_2R_8$, $C(O)R_9$, $S(O)_mR_{10}$ or $NR_{11}R_{12}$ groups, or a 5- or 6-membered heteroaromatic ring optionally substituted with any combination of from one to three halogen, $C_1-C_4$alkyl, $C_1-C_4$haloalkyl, $C_1-C_4$alkoxy, $C_1-C_4$haloalkoxy, cyano, nitro, $CO_2R_8$, $C(O)R_9$, $S(O)_mR_{10}$ or $NR_{11}R_{12}$ groups;

m and n are each independently an integer of 0, 1 or 2;

$R_3$ and $R_8$ are each independently hydrogen, $C_1-C_4$alkyl, benzyl, phenyl or an alkali metal, alkaline earth metal, manganese, copper, zinc, cobalt, silver or nickel cation;

$R_4$ and $R_9$ are each independently hydrogen, $C_1-C_4$alkyl, benzyl or phenyl;

$R_5$ and $R_{10}$ are each independently $C_1-C_4$alkyl or $C_1-C_4$haloalkyl; and $R_6$, $R_7$, $R_{11}$ and $R_{12}$ are each independently hydrogen, $C_1-C_4$alkyl, phenyl or benzyl, and the optical isomers thereof, and the cis and trans isomers thereof.

2. The compound according to claim 1 wherein

Ar is phenyl optionally substituted with any combination of from one to three halogen, $C_1-C_4$alkyl, $C_1-C_4$haloalkyl, $C_1-C_4$alkoxy or $C_1-C_4$haloalkoxy groups;

R and $R_1$ are each independently $C_1-C_4$alkyl;

$R_2$ is hydrogen, cyano, $C_1-C_4$alkyl, $C_1-C_4$haloalkyl, $C_1-C_4$alkoxy, $C_1-C_4$haloalkoxy or fluorine; and $Ar_1$ is 3-phenoxyphenyl optionally substituted with any combination of from one to five halogen, $C_1-C_4$alkyl, $C_1-C_4$haloalkyl, $C_1-C_4$alkoxy or $C_1-C_4$haloalkoxy groups, phenyl optionally substituted with any combination of from one to three halogen, $C_1-C_4$alkyl, $C_1-C_4$haloalkyl, $C_1-C_4$alkoxy or $C_1-C_4$haloalkoxy groups, or biphenyl optionally substituted with any combination of from one to five halogen, $C_1-C_4$alkyl, $C_1-C_4$haloalkyl, $C_1-C_4$alkoxy or $C_1-C_4$haloalkoxy groups.

3. The compound according to claim 2 wherein

R and $R_1$ are methyl;

$R_2$ is hydrogen; and $Ar_1$ is 3-phenoxyphenyl optionally substituted with any combination of from one to five halogen, $C_1-C_4$alkyl, $C_1-C_4$haloalkyl, $C_1-C_4$alkoxy or $C_1-C_4$haloalkoxy groups.

4. The compound according to claim 2 selected from the group consisting of

1-[(p-chlorophenyl)dimethylsilyl]-1,2-difluoro-3-(m-phenoxyphenyl)-1-propene, (Z)-;

1-[(p-chlorophenyl)dimethylsilyl]-1,2-difluoro-3-(4-fluoro-3-phenoxyphenyl)-1-propene, (Z)-;

1-[(p-ethoxyphenyl)dimethylsilyl]-1,2-difluoro-3-(m-phenoxyphenyl)-1-propene, (Z)-;

1-[(p-ethoxyphenyl)dimethylsilyl]-1,2-difluoro-3-(4-fluoro-3-phenoxyphenyl)-1-propene, (Z)-;

1-[(p-ethoxyphenyl)dimethylsilyl]-1,2-difluoro-3-(2-methyl-3-biphenylyl)-1-propene, (Z)-;

1,2-difluoro-1-[(p-fluorophenyl)dimethylsilyl]-3-(m-phenoxyphenyl)-1-propene, (Z)-;

3-[3-(p-chlorophenoxy)phenyl]-1-[(p-ethoxyphenyl) dimethylsilyl]-1,2-difluoro-1-propene, (Z)-; and 1,2-difluoro-3-(4-fluoro-3-phenoxyphenyl)-1-[(p-fluorophenyl)dimethylsilyl]-1-propene, (Z)-.

5. A composition for the control of insect or acarid pests which comprises an agronomically acceptable carrier and a pesticidally effective amount of a compound having the structural formula

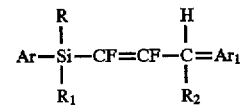

wherein Ar, $Ar_1$, R, $R_1$ and $R_2$ are as described in claim 1.

6. The composition according to claim 5 wherein

Ar is phenyl optionally substituted with any combination of from one to three halogen, $C_1-C_4$alkyl, $C_1-C_4$haloalkyl, $C_1-C_4$alkoxy or $C_1-C_4$haloalkoxy groups;

R and $R_1$ are each independently $C_1-C_4$alkyl;

$R_2$ is hydrogen, cyano, $C_1-C_4$alkyl, $C_1-C_4$haloalkyl, $C_1-C_4$alkoxy, $C_1-C_4$haloalkoxy or fluorine; and $Ar_1$ is 3-phenoxyphenyl optionally substituted with any combination of from one to five halogen, $C_1-C_4$alkyl, $C_1-C_4$haloalkyl, $C_1-C_4$alkoxy or $C_1-C_4$haloalkoxy groups, phenyl optionally substituted with any combination of from one to three halogen, $C_1-C_4$alkyl, $C_1-C_4$haloalkyl, $C_1-C_4$alkoxy or $C_1-C_4$haloalkoxy groups, or biphenyl optionally substituted with any combination of from one to five halogen, $C_1-C_4$alkyl, $C_1-C_4$haloalkyl, $C_1-C_4$alkoxy or $C_1-C_4$haloalkoxy groups.

7. The composition according to claim 6 wherein

R and $R_1$ are methyl;

$R_2$ is hydrogen; and $Ar_1$ is 3-phenoxyphenyl optionally substituted with any combination of from one to five halogen, $C_1-C_4$alkyl, $C_1-C_4$haloalkyl, $C_1-C_4$alkoxy or $C_1-C_4$haloalkoxy groups.

8. The composition according to claim 6 wherein the compound is selected from the group consisting of 1-[(p-chlorophenyl)dimethylsilyl]-1,2-difluoro-3-(m-phenoxyphenyl)-1-propene, (Z)-;

1-[(p-chlorophenyl)dimethylsilyl]-1,2-difluoro-3-(4-fluoro-3-phenoxyphenyl)-1-propene, (Z)-;

1-[(p-ethoxyphenyl)dimethylsilyl]-1,2-difluoro-3-8 (m-phenoxyphenyl)-1-propene, (Z)-;

1-[(p-ethoxyphenyl)dimethylsilyl]-1,2-difluoro-3-(4-fluoro-3-phenoxyphenyl)-1-propene, (Z)-;

1-[(p-ethoxyphenyl)dimethylsilyl]-1,2-difluoro-3-(2-methyl-3-biphenylyl)-1-propene, (Z)-;

1,2-difluoro-1-[(p-fluorophenyl)dimethylsilyl]-3-(m-phenoxyphenyl)-1-propene, (Z)-;

3-[3-(p-chlorophenoxy)phenyl]-1-[(p-ethoxyphenyl) dimethylsilyl]-1,2-difluoro-1-propene, (Z)-; and 1,2-difluoro-3-(4-fluoro-3-phenoxyphenyl)-1-[(p-fluorophenyl)dimethylsilyl]-1-propene, (Z)-.

9. A method for the control of insect or acarid pests which comprises contacting said pests or their food supply, habitat or breeding grounds with a pesticidally effective amount of a compound having the structural formula

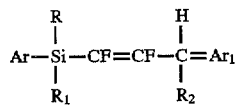

wherein Ar, Ar$_1$, R, R$_1$ and R$_2$ are as described in claim 1.

10. The method according to claim 9 wherein

Ar is phenyl optionally substituted with any combination of from one to three halogen, C$_1$-C$_4$alkyl, C$_1$-C$_4$haloalkyl, C$_1$-C$_4$alkoxy or C$_1$-C$_4$haloalkoxy groups;

R and R$_1$ are each independently C$_1$-C$_4$alkyl;

R$_2$ is hydrogen, cyano, C$_1$-C$_4$alkyl, C$_1$-C$_4$haloalkyl, C$_1$-C$_4$alkoxy, C$_1$-C$_4$haloalkoxy or fluorine; and Ar$_1$ is 3-phenoxyphenyl optionally substituted with any combination of from one to five halogen, C$_1$-C$_4$alkyl, C$_1$-C$_4$haloalkyl, C$_1$-C$_4$alkoxy or C$_1$-C$_4$haloalkoxy groups, phenyl optionally substituted with any combination of from one to three halogen, C$_1$-C$_4$alkyl, C$_1$-C$_4$haloalkyl, C$_1$-C$_4$alkoxy or C$_1$-C$_4$haloalkoxy groups, or biphenyl optionally substituted with any combination of from one to five halogen, C$_1$-C$_4$alkyl, C$_1$-C$_4$haloalkyl, C$_1$-C$_4$alkoxy or C$_1$-C$_4$haloalkoxy groups.

11. The method according to claim 10 wherein

R and R$_1$ are methyl;

R$_2$ is hydrogen; and

Ar$_1$ is 3-phenoxyphenyl optionally substituted with any combination of from one to five halogen, C$_1$-C$_4$alkyl, C$_1$-C$_4$haloalkyl, C$_1$-C$_4$alkoxy or C$_1$-C$_4$haloalkoxy groups.

12. The method according to claim 10 wherein the compound is selected from the group consisting of 1-[(p-chlorophenyl)dimethylsilyl]-1,2-difluoro-3-(m-phenoxyphenyl)-1-propene, (Z)-;

1-[(p-chlorophenyl)dimethylsilyl]-1,2-difluoro-3-(4-fluoro-3-phenoxyphenyl)-1-propene, (Z)-;

1-[(p-ethoxyphenyl)dimethylsilyl]-1,2-difluoro-3-(m-phenoxyphenyl)-1-propene, (Z)-;

1-[(p-ethoxyphenyl)dimethylsilyl]-1,2-difluoro-3-(4-fluoro-3-phenoxyphenyl)-1-propene, (Z)-;

1-[(p-ethoxyphenyl)dimethylsilyl]-1,2-difluoro-3-(2-methyl-3-biphenylyl)-1-propene, (Z)-;

1,2-difluoro-1-[(p-fluorophenyl)dimethylsilyl]-3-(m-phenoxyphenyl)-1-propene, (Z)-;

3-[3-(p-chlorophenoxy)phenyl]-1-[(p-ethoxyphenyl)dimethylsilyl]-1,2-difluoro-1-propene, (Z)-; and 1,2-difluoro-3-(4-fluoro-3-phenoxyphenyl)-1-[(p-fluorophenyl)dimethylsilyl]-1-propene, (Z)-.

13. A method for the protection of growing plants from attack or infestation by insect or acarid pests which comprises applying to the foliage of the plants, or to the soil or water in which they are growing, a pesticidally effective amount of a compound having the structural formula

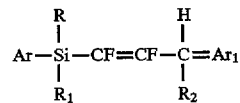

wherein Ar, Ar$_1$, R, R$_1$ and R$_2$ are as described in claim 1.

14. The method according to claim 13 wherein

Ar is phenyl optionally substituted with any combination of from one to three halogen, C$_1$-C$_4$alkyl, C$_1$-C$_4$haloalkyl, C$_1$-C$_4$alkoxy or C$_1$-C$_4$haloalkoxy groups;

R and R$_1$ are each independently C$_1$-C$_4$alkyl;

R$_2$ is hydrogen, cyano, C$_1$-C$_4$alkyl, C$_1$-C$_4$haloalkyl, C$_1$-C$_4$alkoxy, C$_1$-C$_4$haloalkoxy or fluorine; and Ar$_1$ is 3-phenoxyphenyl optionally substituted with any combination of from one to five halogen, C$_1$-C$_4$alkyl, C$_1$-C$_4$haloalkyl, C$_1$-C$_4$alkoxy or C$_1$-C$_4$haloalkoxy groups, phenyl optionally substituted with any combination of from one to three halogen, C$_1$-C$_4$alkyl, C$_1$-C$_4$haloalkyl, C$_1$-C$_4$alkoxy or C$_1$-C$_4$haloalkoxy groups, or biphenyl optionally substituted with any combination of from one to five halogen, C$_1$-C$_4$alkyl, C$_1$-C$_4$haloalkyl, C$_1$-C$_4$alkoxy or C$_1$-C$_4$haloalkoxy groups.

15. The method according to claim 14 wherein

R and R$_1$ are methyl;

R$_2$ is hydrogen; and

Ar$_1$ is 3-phenoxyphenyl optionally substituted with any combination of from one to five halogen, C$_1$-C$_4$alkyl, C$_1$-C$_4$haloalkyl, C$_1$-C$_4$alkoxy or C$_1$-C$_4$haloalkoxy groups.

16. The method according to claim 14 wherein the compound is selected from the group consisting of 1-[(p-chlorophenyl)dimethylsilyl]-1,2-difluoro-3-(m-phenoxyphenyl)-1-propene, (Z)-;

1-[(p-chlorophenyl)dimethylsilyl]-1,2-difluoro-3-(4-fluoro-3-phenoxyphenyl)-1-propene, (Z)-;

1-[(p-ethoxyphenyl)dimethylsilyl]-1,2-difluoro-3-(m-phenoxyphenyl)-1-propene, (Z)-;

1-[(p-ethoxyphenyl)dimethylsilyl]-1,2-difluoro-3-(4-fluoro-3-phenoxyphenyl)-1-propene, (Z)-;

1-[(p-ethoxyphenyl)dimethylsilyl]-1,2-difluoro-3-(2-methyl-3-biphenylyl)-1-propene, (Z)-;

1,2-difluoro-1-[(p-fluorophenyl)dimethylsilyl]-3-(m-phenoxyphenyl)-1-propene, (Z)-;

3-[3-(p-chlorophenoxy)phenyl]-1-[(p-ethoxyphenyl)dimethylsilyl]-1,2-difluoro-1-propene, (Z)-; and 1,2-difluoro-3-(4-fluoro-3-phenoxyphenyl)-1-[(p-fluorophenyl)dimethylsilyl]-1-propene, (Z)-.

17. The method according to claim 13 wherein the compound is applied to the plants, or to the soil or water in which they are growing, at a rate of about 0.1 kg/ha to 4.0 kg/ha.

* * * * *

UNITED STATES PATENT AND TRADEMARK OFFICE
CERTIFICATE OF CORRECTION

PATENT NO. : 5,710,102
DATED : January 20, 1998
INVENTOR(S) : Keith Douglas Barnes, et al.

It is certified that error appears in the above-identified patent and that said Letters Patent is hereby corrected as shown below:

On the title page item [57],

In the abstract, on line 3, change "=$Ar_1$" to "-$Ar_1$".

In column 5, on line 31, change "ZNCl" to "ZnCl".

In column 1, line 39, change "=$Ar_1$" to "-$Ar_1$".

In column 3, line 18, change "=$Ar_1$" to "-$Ar_1$".

In column 12, line 3, change "=$Ar_1$" to "-$Ar_1$".

In column 14, line 15, change "=$Ar_1$" to "-$Ar_1$".

In column 15, line 3, change "=$Ar_1$" to "-$Ar_1$".

In column 16, line 1, change "=$Ar_1$" to "-$Ar_1$".

Signed and Sealed this

Twenty-eighth Day of April, 1998

Attest:

Attesting Officer

BRUCE LEHMAN

Commissioner of Patents and Trademarks